United States Patent [19]

Jacobs et al.

[11] Patent Number: 5,728,819
[45] Date of Patent: Mar. 17, 1998

[54] SECRETED PROTEINS AND POLYNUCLEOTIDES ENCODING THEM

[75] Inventors: Kenneth Jacobs, Newton; John M. McCoy, Reading; Edward R. LaVallie, Tewksbury; Lisa A. Racie; David Merberg, both of Acton; Maurice Treacy, Chestnut Hill; Cheryl Evans, Brookline; Vikki Spaulding, Billerica, all of Mass.

[73] Assignee: Genetics Institute, Inc., Cambridge, Mass.

[21] Appl. No.: 691,641

[22] Filed: Aug. 2, 1996

[51] Int. Cl.$^6$ .................. C12N 15/12; C12N 15/10; C12N 5/10; C07K 14/435

[52] U.S. Cl. .................. 536/23.5; 435/69.1; 435/325; 435/252.3; 435/254.11; 435/320.1; 530/300; 536/23.1; 514/12

[58] Field of Search .................. 435/69.1, 325, 435/252.3, 254.11, 320.1; 424/185.1, 278.1, 543, 570; 514/44–46, 2, 12; 530/300, 350, 351, 839; 536/23.1, 26.1, 23.5

[56] References Cited

U.S. PATENT DOCUMENTS 4,267,195  5/1981  Boudreau et al. .................. 426/2

OTHER PUBLICATIONS

Genbank Accession No. T41078.
Genbank Accession No. R52631.
Genbank Accession No. AA019923.
Genbank Accession No. AA013272.
Genbank Accession No. Z73913.
Genbank Accession No. L29074.
Genbank Accession No. Q76950.
Rajakumar et al., Nucleotide sequence of the rhamnose biosynthetic operon of *Shigella flexneri* 2a and role of lipopolysaccharide in virulence, J. Bact., 176(8): 2362–2373, Mar. 1994.

*Primary Examiner*—Stephen Walsh
*Assistant Examiner*—Claire M. Kaufman
*Attorney, Agent, or Firm*—Scott A. Brown; Thomas J. DesRosier

[57] ABSTRACT

Novel polynucleotides and the proteins encoded thereby are disclosed.

21 Claims, No Drawings

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
  ( A ) LENGTH: 205 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:1:

CACAGTAGGT GTATATATTT ATGGACTACA TGANATACAG GCATGCAATG CATAATAATC    60

```
ACATCATGGA  AAATTGGGTA  TTCATCACCT  CAAGCATTTA  TCCTTTGTGT  TACANATAAT      120

CCACTTCTAC  TCTTTTACTT  ATTTTAAAGT  GTNCAATTAA  ACTATGATTG  ACTATAGTCT      180

CCTTGTTGTG  CTGTCACATA  CTATG                                               205
```

( 2 ) INFORMATION FOR SEQ ID NO:2:

( i ) SEQUENCE CHARACTERISTICS:
        ( A ) LENGTH: 424 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

```
TACNNGACNN  GNGTTATTNT  TATNATTGCA  TGGNGGAGCA  TGGACATAAT  TTCTACTGCA       60

GCTGAGCATT  TTTTAATATG  GATAATAGGA  TTCTGCAAGT  GANACATTTG  GTCAGAGAAC      120

TTAATAAACT  AGTCAAGTGG  GATAGGTCCT  GTGACAGAAT  TGTGTGATAC  AGGTCAAACA      180

GGAGTTGGGT  TATGGGGAAA  ATGCCAGTTG  AAATATGTTT  TGATCTTTGG  AGAAACCTAT      240

TTTTTCATTT  AACCTGTTCT  TTAAATCCAG  TATGTTCCAG  AACATACAAA  AATGTTTAAA      300

TGTTCCATTT  GTAAGAGGAT  ATCATGTATT  TTATATCAAT  TTAAATGCAG  TTATCCTAAT      360

CATTTTCTT   TCATTTTAC   CCTTATTAA   CTCTTCATTT  GTTACAAAA   CAAATCCACT      420

CTAT                                                                        424
```

( 2 ) INFORMATION FOR SEQ ID NO:3:

( i ) SEQUENCE CHARACTERISTICS:
        ( A ) LENGTH: 51 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:3:

```
Met  Phe  Gln  Asn  Ile  Gln  Lys  Cys  Leu  Asn  Val  Pro  Phe  Val  Arg  Gly
 1                   5                        10                       15

Tyr  His  Val  Phe  Tyr  Ile  Asn  Leu  Asn  Ala  Val  Ile  Leu  Ile  Ile  Phe
               20                        25                       30

Leu  Ser  Phe  Leu  Pro  Phe  Ile  Asn  Ser  Ser  Phe  Val  Tyr  Lys  Thr  Asn
          35                        40                       45

Pro  Leu  Tyr
     50
```

( 2 ) INFORMATION FOR SEQ ID NO:4:

( i ) SEQUENCE CHARACTERISTICS:
        ( A ) LENGTH: 247 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

```
TCAGAAATAA  ATTTAAAAGA  CGTTTGTAAC  CACTGTGTTT  TATTTACTGT  GTGTTGTGGT       60

GGCCTGTTGG  AGGCAAATAG  ATCAGATTTT  TTTTGNACCT  ACGTAAGAGT  ACTTGAAGTT      120

TTATTTAAAA  TAAAATGTTG  TGGAAAAGGT  AGCATTCTTT  TTTTAGGAGT  GTTATTTTTC      180

ACTATGTGTG  GCACGGATAC  AATAAAAGAN  TTTACAAAN   TAAAAAAAAA  AAAAAAAAA       240
```

( 2 ) INFORMATION FOR SEQ ID NO:5:

( i ) SEQUENCE CHARACTERISTICS:
        ( A ) LENGTH: 272 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

```
GCCAGCAGTT GTGCCAGCAG CATGCATCCA GCAGGGGTGC TAGGCAAAGA AAAGGTGGGT      60
TGAGGACAGG GCGTGTTCTC CGGGACTCTG TNAGCCACGA NGANGCTGCA ACACCANCCC     120
CANANCCTCC GGGAAATGGG GACTTCCANG ACCANCCACA GCCCCGGGGT GGGGACACTG     180
ACCCNGAGCT CACNAAATAA AGGCCGTCTT GCGGGTTTAT GATATCCTGG GTAACGGCAG     240
CCTTGGGGCT GTTTTTCAAN AAGCTTGCTC TT                                   272
```

( 2 ) INFORMATION FOR SEQ ID NO:6:

( i ) SEQUENCE CHARACTERISTICS:
        ( A ) LENGTH: 509 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

```
AGGAGAATTA GGACAGTTTT TCCTTCTGGC CGCAAGTACG GAGNGANTNA AAAATGTGAG      60
ACACTTTCTT NGGCTGCAAA TNTGACTGAT TTCCATTTTA ANGAGAAAGT CCACATTTCT     120
GATCANACAT TTTTTCTTGT AAAGACAGAC TTAGGNGCTT TTCTCCTCTA TGTTTTTGTG     180
GCATAATTTT TCATAAGGAA AGTATATTTA TGATATTTAC ATTAATATAA TTAATGTATA     240
TTTTATATTA GTAGCATATT AACAGTGTAA TAAAAAATAA AAACAAACTC TAGTATCCAG     300
AGGATCACAT GCTGACCAGA CCCTGTGTAG AAAGTGCCGA AGAGCATCAA GGAAATGGAA     360
ACGTTGGAAT TCCATCCGTG CTTGTGGCTT TCCTTAAACT TTTGTTATGG AAAATTTCAA     420
ATATACCCCG AAGTGGAGAT TGGCTTAAAT CAGCCCCACG TGCCCATCAC TCGGCTCCAG     480
TCATTATCCA GTGTGGTTCC TCTGATCTT                                       509
```

( 2 ) INFORMATION FOR SEQ ID NO:7:

( i ) SEQUENCE CHARACTERISTICS:
        ( A ) LENGTH: 67 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:7:

```
Met Leu Thr Arg Pro Cys Val Glu Ser Ala Glu Glu His Gln Gly Asn
 1               5                  10                  15

Gly Asn Val Gly Ile Pro Ser Val Leu Val Ala Phe Leu Lys Leu Leu
             20                  25                  30

Leu Trp Lys Ile Ser Asn Ile Pro Arg Ser Gly Asp Trp Leu Lys Ser
         35                  40                  45

Ala Pro Arg Ala His His Ser Ala Pro Val Ile Ile Gln Cys Gly Ser
```

Ser Asp Leu
65

( 2 ) INFORMATION FOR SEQ ID NO:8:

( i ) SEQUENCE CHARACTERISTICS:
        ( A ) LENGTH: 264 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:8:

```
TGGCAGCAAT GAGATCTGCT NTCTTAATTC TGTGCNGGGA AATCTTCNGG CGNGAATGGG      60
TTTGAGGCTT GAAACATNAC TTATATAAGT CACCTAAACN ACAAAACAAN GATTGGAGTA     120
AAAATTAATG CCATTTTTAT TTAAGTATC  AGATACCAGA TGATGCATGT CAACTAAGCT     180
TTTAGCTTTT CTTAAAAGAT GCAAAGGTTT CAAANCCAAA AATATTTAAT AAAAATAAAC     240
CCAACATAAA AAAAAAAAA  AAAA                                           264
```

( 2 ) INFORMATION FOR SEQ ID NO:9:

( i ) SEQUENCE CHARACTERISTICS:
        ( A ) LENGTH: 210 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:9:

```
GCGGCCGCGG GTGCGCTTCT CNGCGGGGCC AGGCAAGGCC NTCTCCTGTC GNTTAGGACN      60
CGCTCCCGGG GCNGGCGCTA TGGTCACNAA CTNAGGCGGC CGGACAACCG GCNNAACCNA     120
NAATGNCNGA TCNACCGCAC GNCNNCNCCN CNCCCATCTT NTGTNCAGAT CCCCTTNCCA     180
CGGNTAATCT CCATGGCCTC ACCGTGTCTT                                     210
```

( 2 ) INFORMATION FOR SEQ ID NO:10:

( i ) SEQUENCE CHARACTERISTICS:
        ( A ) LENGTH: 500 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:10:

```
AACCATTATA AGCTGCAATA AACAAGTTAA NTNTAGANTC GAGCGGCCGC GGGTGCGTTT      60
TCGGCGGGGC CGGGCAGGGC CGTCGCCTGG CGGTGAGGAC GCGNTCCCGG GGCGGGCGNT     120
ATGGCCACCA ANTAGGGCGG CCGGAGAAGC GGCCGAAGCC CAAGATGCCG GAGCGACGGC     180
ACGGNTGCGC CTCCGCCATN GTAGGTGCCG ATCCCCTTGC CACAGTCGAG TNTCCATGGC     240
CTGACCGTGT NTTGACAATA ATTTTGAGCA AAATNTATGT CTAATAAGAA GATAACCACA     300
TCAAGATGGT TGGGAAGCTG AAGCAGAACT TACTCTTGGC GTGTCTGGTG ATTAGTTCTG     360
TGACCGTGTT TTACCTGGGC CAGCATGCCA TGGAGTGCCA TCACCGAATA GAGGAACGTA     420
GCCAGCCAGC CCGACTGGAG AACCCCAAGG CGACTGTGCG AGCTGGCCTC GACATCAAAG     480
CCAACAAAAC ATTCACCTAT                                                500
```

( 2 ) INFORMATION FOR SEQ ID NO:11:

( i ) SEQUENCE CHARACTERISTICS:
        ( A ) LENGTH: 65 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:11:

```
Met Val Gly Lys Leu Lys Gln Asn Leu Leu Leu Ala Cys Leu Val Ile
 1               5                  10                  15
Ser Ser Val Thr Val Phe Tyr Leu Gly Gln His Ala Met Glu Cys His
            20                  25                  30
His Arg Ile Glu Glu Arg Ser Gln Pro Ala Arg Leu Glu Asn Pro Lys
        35                  40                  45
Ala Thr Val Arg Ala Gly Leu Asp Ile Lys Ala Asn Lys Thr Phe Thr
    50                  55                  60
Tyr
65
```

( 2 ) INFORMATION FOR SEQ ID NO:12:

( i ) SEQUENCE CHARACTERISTICS:
        ( A ) LENGTH: 118 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:12:

```
CATTGTATTG TTTCAGAGAC GTACCNAAAT TACTGTATAC ATNTACAACN TAATGAATAC        60
CGTANCTTAN NNTTCAAAAT CAAAGTTNNA ATGTGNANCA CTCAAANAAN AAAAAAA         118
```

( 2 ) INFORMATION FOR SEQ ID NO:13:

( i ) SEQUENCE CHARACTERISTICS:
        ( A ) LENGTH: 192 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:13:

```
CTTTGCGAAA GCATGGCGGC CACTTTGTGA GTGTCCGCAA GACGGTTAAA TAGGGCATTT         60
TAATTCAAGA GAGGAATAAG AAAAGTGGTA CCTAACATCT CTTATAGATT ATTTTCATCT        120
TGATATCCGC CTAACACAAT GCTTAATATC CGCCTGAGTG TGTGGATTAC AAACCTTTAG       180
AAGTTGCGGT CC                                                          192
```

( 2 ) INFORMATION FOR SEQ ID NO:14:

( i ) SEQUENCE CHARACTERISTICS:
        ( A ) LENGTH: 478 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:14:

```
TTTTNTNNTT TTTACAGCAT GCGGAGAAGT TGCACGGTCC TTGGNCAGGC AGTTGTTCCC        60
```

```
ANATTTTGNT  TCACCAAAGC  TTGCTTTAAA  ANTNACCCTT  TGAGATGGGG  GNTGNGAGAG      120

CAGAAGATAA  CATACAACCT  AGAACTNTCC  CTTNGGTTNA  CCCAGAAAAC  TTTTTTGGAC      180

ACAAGGACCG  GACCCCCGGA  AAGCAAAGGA  GGATAGTACC  AAGCAAGTGT  CTATTCGCAG      240

AAATCAAAGA  GAGGAAACCG  GCGTCTCAAT  GTCTCAGAAA  GTGAGAGAAG  CTGGGAGAGA      300

CGTCAGCTAC  TTGATAGTGG  TGCTCTTTGG  AGTCGGCCTT  ACAGGCGGCT  TGTTATACGC      360

GATCTTCAAA  GAACTGTTTT  TTTCGTCCAG  CCCTAATATC  ATATATGGGA  AAGCCTTAGG      420

AAAATGCAGA  ACACACCCTG  AGGTGATTGG  TGTATTTGGT  GAGCCTTTGA  AAGGCTAC       478
```

(2) INFORMATION FOR SEQ ID NO:15:

(i) SEQUENCE CHARACTERISTICS:
        (A) LENGTH: 70 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

```
Met  Ser  Gln  Lys  Val  Arg  Glu  Ala  Gly  Arg  Asp  Val  Ser  Tyr  Leu  Ile
 1              5                        10                       15

Val  Val  Leu  Phe  Gly  Val  Gly  Leu  Thr  Gly  Gly  Leu  Leu  Tyr  Ala  Ile
              20                        25                       30

Phe  Lys  Glu  Leu  Phe  Phe  Ser  Ser  Pro  Asn  Ile  Ile  Tyr  Gly  Lys
         35                        40                       45

Ala  Leu  Gly  Lys  Cys  Arg  Thr  His  Pro  Glu  Val  Ile  Gly  Val  Phe  Gly
     50                        55                       60

Glu  Pro  Leu  Lys  Gly  Tyr
 65                      70
```

(2) INFORMATION FOR SEQ ID NO:16:

(i) SEQUENCE CHARACTERISTICS:
        (A) LENGTH: 168 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:16:

```
ATTTCAGCTC  TACCTTCATG  ATAAACTTTT  GTTACTAAAA  TTTATATACA  CACATAAGTA       60

AAGTTTTAAG  TATTTTATGC  TGTTTAATGT  TGTGTGGCTT  TTATACAATC  TACAGAATAA      120

AGAAAACTAA  CTAGAAGATG  TTAAAAGCAA  AAAAAAAAA  AAAAAAA                      168
```

(2) INFORMATION FOR SEQ ID NO:17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="oligonucleotide"

(xi) SEQUENCE DESCRIPTION: SEQ ID NO:17:

```
TNTGGAACAT  ACTGGATTTA  AAGAACAGG                                            29
```

(2) INFORMATION FOR SEQ ID NO:18:

(i) SEQUENCE CHARACTERISTICS:
   (A) LENGTH: 29 base pairs
   (B) TYPE: nucleic acid
   (C) STRANDEDNESS: single
   (D) TOPOLOGY: linear (ii) MOLECULE TYPE: other nucleic acid
   (A) DESCRIPTION: /desc ="oligonucleotide"

(xi) SEQUENCE DESCRIPTION: SEQ ID NO:18:

ANAGTTTAAG GAAAGCCACA AGCACGGAT                               29

(2) INFORMATION FOR SEQ ID NO:19:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc ="oligonucleotide"

(xi) SEQUENCE DESCRIPTION: SEQ ID NO:19:

TNCGTTCCTC TATTCGGTGA TGGCACTCC                               29

(2) INFORMATION FOR SEQ ID NO:20:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc ="oligonucleotide"

(xi) SEQUENCE DESCRIPTION: SEQ ID NO:20:

ANAGAGCACC ACTATCAAGT AGCTGACGT                               29

SECRETED PROTEINS AND POLYNUCLEOTIDES ENCODING THEM

FIELD OF THE INVENTION

The present invention provides novel polynucleotides and proteins encoded by such polynucleotides, along with therapeutic, diagnostic and research utilities for these polynucleotides and proteins.

BACKGROUND OF THE INVENTION

Technology aimed at the discovery of protein factors (including e.g., cytokines, such as lymphokines, interferons, CSFs and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for proteins that are known to have biological activity by virtue of their secreted nature in the case of leader sequence cloning, or by virtue of the cell or tissue source in the case of PCR-based techniques. It is to these proteins and the polynucleotides encoding them that the present invention is directed.

SUMMARY OF THE INVENTION

In one embodiment, the present invention provides a composition comprising an isolated polynucleotide selected from the group consisting of:

(a) a polynucleotide comprising the nucleotide sequence of SEQ ID NO:2;

(b) a polynucleotide comprising the nucleotide sequence of SEQ ID NO:2 from nucleotide 272 to nucleotide 424;

(c) a polynucleotide comprising the nucleotide sequence of SEQ ID NO:2 from nucleotide 395 to nucleotide 424;

(d) a polynucleotide comprising the nucleotide sequence of the full length protein coding sequence of clone BG511_30 deposited under accession number ATCC 98117;

(e) a polynucleotide encoding the full length protein encoded by the cDNA insert of clone BG511_30 deposited under accession number ATCC 98117;

(f) a polynucleotide comprising the nucleotide sequence of the mature protein coding sequence of clone BG511_30 deposited under accession number ATCC 98117;

(g) a polynucleotide encoding the mature protein encoded by the cDNA insert of clone BG511_30 deposited under accession number ATCC 98117;

(h) a polynucleotide encoding a protein comprising the amino acid sequence of SEQ ID NO:3;

(i) a polynucleotide encoding a protein comprising a fragment of the amino acid sequence of SEQ ID NO:3 having biological activity;

(j) a polynucleotide which is an allelic variant of a polynucleotide of (a)–(g) above;

(k) a polynucleotide which encodes a species homologue of the protein of (h) or (i) above.

Preferably, such polynucleotide comprises the nucleotide sequence of SEQ ID NO:2 from nucleotide 272 to nucleotide 424; the nucleotide sequence of SEQ ID NO:2 from nucleotide 395 to nucleotide 424; the nucleotide sequence of the full length protein coding sequence of clone BG511_30 deposited under accession number ATCC 98117; or the nucleotide sequence of the mature protein coding sequence of clone BG511_30 deposited under accession number ATCC 98117. In other preferred embodiments, the polynucleotide encodes the full length or mature protein encoded by the cDNA insert of clone BG511_30 deposited under accession number ATCC 98117.

Other embodiments provide the gene corresponding to the cDNA sequence of SEQ ID NO:2, SEQ ID NO:1 or SEQ ID NO:4.

In other embodiments, the present invention provides a composition comprising a protein, wherein said protein comprises an amino acid sequence selected from the group consisting of:

(a) the amino acid sequence of SEQ ID NO:3;

(b) fragments of the amino acid sequence of SEQ ID NO:3; and (c) the amino acid sequence encoded by the cDNA insert of clone BG511_30 deposited under accession number ATCC98117; the protein being substantially free from other mammalian proteins. Preferably such protein comprises the amino acid sequence of SEQ ID NO:3.

In one embodiment, the present invention provides a composition comprising an isolated polynucleotide selected from the group consisting of:

(a) a polynucleotide comprising the nucleotide sequence of SEQ ID NO:6;

(b) a polynucleotide comprising the nucleotide sequence of SEQ ID NO:6 from nucleotide 309 to nucleotide 509;

(c) a polynucleotide comprising the nucleotide sequence of the full length protein coding sequence of clone BL15_1 deposited under accession number ATCC 98117;

(d) a polynucleotide encoding the full length protein encoded by the cDNA insert of clone BL15_1 deposited under accession number ATCC 98117;

(e) a polynucleotide comprising the nucleotide sequence of the mature protein coding sequence of clone BL15_1 deposited under accession number ATCC 98117;

(f) a polynucleotide encoding the mature protein encoded by the cDNA insert of clone BL15_1 deposited under accession number ATCC 98117;

(g) a polynucleotide encoding a protein comprising the amino acid sequence of SEQ ID NO:7;

(h) a polynucleotide encoding a protein comprising a fragment of the amino acid sequence of SEQ ID NO:7 having biological activity;

(i) a polynucleotide which is an allelic variant of a polynucleotide of (a)–(d) above;

(j) a polynucleotide which encodes a species homologue of the protein of (g) or (h) above.

Preferably, such polynucleotide comprises the nucleotide sequence of SEQ ID NO:6 from nucleotide 309 to nucleotide 509; the nucleotide sequence of the full length protein coding sequence of clone BL15_1 deposited under accession number ATCC 98117; or the nucleotide sequence of the mature protein coding sequence of clone BL15_1 deposited under accession number ATCC 98117. In other preferred embodiments, the polynucleotide encodes the full length or mature protein encoded by the cDNA insert of clone BL15_1 deposited under accession number ATCC 98117.

Other embodiments provide the gene corresponding to the cDNA sequence of SEQ ID NO:6, SEQ ID NO:5 or SEQ ID NO:8.

In other embodiments, the present invention provides a composition comprising a protein, wherein said protein comprises an amino acid sequence selected from the group consisting of:

(a) the amino acid sequence of SEQ ID NO:7;

(b) fragments of the amino acid sequence of SEQ ID NO:7; and (c) the amino acid sequence encoded by the cDNA insert of clone BL15_1 deposited under accession number ATCC98117; the protein being substantially free from other mammalian proteins. Preferably such protein comprises the amino acid sequence of SEQ ID NO:7.

In one embodiment, the present invention provides a composition comprising an isolated polynucleotide selected from the group consisting of:

(a) a polynucleotide comprising the nucleotide sequence of SEQ ID NO:10;

(b) a polynucleotide comprising the nucleotide sequence of SEQ ID NO:10 from nucleotide 306 to nucleotide 500;

(c) a polynucleotide comprising the nucleotide sequence of SEQ ID NO:10 from nucleotide 366 to nucleotide 500;

(d) a polynucleotide comprising the nucleotide sequence of the full length protein coding sequence of clone K289_3 deposited under accession number ATCC 98117;

(e) a polynucleotide encoding the full length protein encoded by the cDNA insert of clone K289_3 deposited under accession number ATCC 98117;

(f) a polynucleotide comprising the nucleotide sequence of the mature protein coding sequence of clone K289_3 deposited under accession number ATCC 98117;

(g) a polynucleotide encoding the mature protein encoded by the cDNA insert of clone K289_3 deposited under accession number ATCC 98117;

(h) a polynucleotide encoding a protein comprising the amino acid sequence of SEQ ID NO:11;

(i) a polynucleotide encoding a protein comprising a fragment of the amino acid sequence of SEQ ID NO:11 having biological activity;

(j) a polynucleotide which is an allelic variant of a polynucleotide of (a)–(g) above;

(k) a polynucleotide which encodes a species homologue of the protein of (h) or (i) above.

Preferably, such polynucleotide comprises the nucleotide sequence of SEQ ID NO:10 froth nucleotide 306 to nucleotide 500; the nucleotide sequence of SEQ ID NO:10 from nucleotide 366 to nucleotide 500; the nucleotide sequence of the full length protein coding sequence of clone K289_3 deposited under accession number ATCC 98117; or the nucleotide sequence of the mature protein coding sequence of clone K289_3 deposited under accession number ATCC 98117. In other preferred embodiments, the polynucleotide encodes the full length or mature protein encoded by the cDNA insert of clone K289_3 deposited under accession number ATCC 98117.

Other embodiments provide the gene corresponding to the cDNA sequence of SEQ ID NO:10, SEQ ID NO:9 or SEQ ID NO:12.

In other embodiments, the present invention provides a composition comprising a protein, wherein said protein comprises an amino acid sequence selected from the group consisting of:

(a) the amino acid sequence of SEQ ID NO:11;

(b) fragments of the amino acid sequence of SEQ ID NO:11; and (c) the amino acid sequence encoded by the cDNA insert of clone K289_3 deposited under accession number ATCC98117;

the protein being substantially free from other mammalian proteins. Preferably such protein comprises the amino acid sequence of SEQ ID NO:11.

In one embodiment, the present invention provides a composition comprising an isolated polynucleotide selected from the group consisting of:

(a) a polynucleotide comprising the nucleotide sequence of SEQ ID NO:14;

(b) a polynucleotide comprising the nucleotide sequence of SEQ ID NO:14 from nucleotide 269 to nucleotide 478;

(c) a polynucleotide comprising the nucleotide sequence of SEQ ID NO:14 from nucleotide 350 to nucleotide 478;

(d) a polynucleotide comprising the nucleotide sequence of the full length protein coding sequence of clone K322_2 deposited under accession number ATCC 98117;

(e) a polynucleotide encoding the full length protein encoded by the cDNA insert of clone K322_2 deposited under accession number ATCC 98117;

(f) a polynucleotide comprising the nucleotide sequence of the mature protein coding sequence of clone K322_2 deposited under accession number ATCC 98117;

(g) a polynucleotide encoding the mature protein encoded by the cDNA insert of clone K322_2 deposited under accession number ATCC 98117;

(h) a polynucleotide encoding a protein comprising the amino acid sequence of SEQ ID NO:15;

(i) a polynucleotide encoding a protein comprising a fragment of the amino acid sequence of SEQ ID NO:15 having biological activity;

(j) a polynucleotide which is an allelic variant of a polynucleotide of (a)–(g) above;

(k) a polynucleotide which encodes a species homologue of the protein of (h) or (i) above.

Preferably, such polynucleotide comprises the nucleotide sequence of SEQ D NO:14 from nucleotide 269 to nucleotide 478; the nucleotide sequence of SEQ D NO:14 from nucleotide 350 to nucleotide 478; the nucleotide sequence of the full length protein coding sequence of clone K322_2 deposited under accession number ATCC 98117; or the nucleotide sequence of the mature protein coding sequence of clone K322_2 deposited under accession number ATCC 98117. In other preferred embodiments, the polynucleotide encodes the full length or mature protein encoded by the cDNA insert of clone K322_2 deposited under accession number ATCC 98117.

Other embodiments provide the gene corresponding to the cDNA sequence of SEQ ID NO:14, SEQ D NO:13 or SEQ D NO:16.

In other embodiments, the present invention provides a composition comprising a protein, wherein said protein comprises an amino acid sequence selected from the group consisting of:

(a) the amino acid sequence of SEQ D NO:15;

(b) fragments of the amino acid sequence of SEQ D NO:15; and (c) the amino acid sequence encoded by the cDNA insert of clone K322_2 deposited under accession number ATCC98117; the protein being substantially free from other mammalian proteins. Preferably such protein comprises the amino acid sequence of SEQ D NO:15.

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing a protein, which comprise:

(a) growing a culture of the host cell transformed with such polynucleotide compositions in a suitable culture medium; and (b) purifying the protein from the culture.

The protein produced according to such methods is also provided by the present invention. Preferred embodiments include those in which the protein produced by such process is a mature form of the protein.

Protein compositions of the present invention may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

DETAILED DESCRIPTION

Isolated Proteins and Polynucleotides

Nucleotide and amino acid sequences are reported below for each clone and protein disclosed in the present application. In some instances the sequences are preliminary and may include some incorrect or ambiguous bases or amino acids. The actual nucleotide sequence of each clone can readily be determined by sequencing of the deposited clone in accordance with known methods. The predicted amino acid sequence (both full length and mature) can then be determined from such nucleotide sequence. The amino acid sequence of the protein encoded by a particular clone can also be determined by expression of the clone in a suitable host cell, collecting the protein and determining its sequence.

For each disclosed protein applicants have identified what they have determined to be the reading frame best identifiable with sequence information available at the time of filing. Because of the partial ambiguity in reported sequence information, reported protein sequences include "Xaa" designators. These "Xaa" designators indicate either (1) a residue which cannot be identified because of nucleotide sequence ambiguity or (2) a stop codon in the determined nucleotide sequence where applicants believe one should not exist (if the nucleotide sequence were determined more accurately).

As used herein a "secreted" protein is one which, when expressed in a suitable host cell, is transported across or through a membrane, including transport as a result of signal sequences in its amino acid sequence. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplpasmic reticulum.

Clone "BG511_30"

A polynucleotide of the present invention has been identified as clone "BG511_30". BG511_30 was isolated from a human adult brain cDNA library using methods which are selective for cDNAs encoding secreted proteins. BG511_30 is a full-length clone, including the entire coding sequence of a secreted protein (also referred to herein as "BG511_30 protein").

The nucleotide sequence of the 5' portion of BG511_30 as presently determined is reported in SEQ ID NO:1. An additional internal nucleotide sequence from BG511_30 as presently determined is reported in SEQ ID NO:2. What applicants believe is the proper reading frame and the predicted amino acid sequence encoded by such internal sequence is reported in SEQ ID NO:3. Amino acids 1 to 41 of SEQ ID NO:3 are a predicted leader/signal sequence, with the predicted mature amino acid sequence beginning at amino acid 42. Additional nucleotide sequence from the 3' portion of BG511_30, including the polyA tail, is reported in SEQ ID NO:4.

The EcoRI/NotI restriction fragment obtainable from the deposit containing clone BG511_30 should be approximately 2250 bp.

The nucleotide sequence disclosed herein for BG511_30 was searched against the GenBank database using BLASTA/BLASTX and FASTA search protocols. BG511_30 demonstrated at least some identity with an EST identified as "ya30c02.s5 Homo sapiens cDNA clone 62114 3'" (T41078, BlastN). Based upon identity, BG511_30 proteins and each identical protein or peptide may share at least some activity.

Clone "BL15_1"

A polynucleotide of the present invention has been identified as clone "BL15_1". BL15_1 was isolated from a human adult testes cDNA library using methods which are selective for cDNAs encoding secreted proteins. BL15_1 is a full-length clone, including the entire coding sequence of a secreted protein (also referred to herein as "BL15_1 protein").

The nucleotide sequence of the 5' portion of BL15_1 as presently determined is reported in SEQ ID NO:5. An additional internal nucleotide sequence from BL15_1 as presently determined is reported in SEQ ID NO:6. What applicants believe is the proper reading frame and the predicted amino acid sequence encoded by such internal sequence is reported in SEQ ID NO:7. Additional nucleotide sequence from the 3' portion of BL15_1, including the polyA tail, is reported in SEQ ID NO:8.

The nucleotide sequence disclosed herein for BL15_1 was searched against the GenBank database using BLASTA/BLASTX and FASTA search protocols. No hits were found in the database.

Clone "K289_3"

A polynucleotide of the present invention has been identified as clone "K289_3". K289_3 was isolated from a murine bone marrow (stromal cell line FCM-4) cDNA library using methods which are selective for cDNAs encoding secreted proteins. K289_3 is a full-length clone, including the entire coding sequence of a secreted protein (also referred to herein as "K289_3 protein").

The nucleotide sequence of the 5' portion of K289_3 as presently determined is reported in SEQ ID NO:9. An additional internal nucleotide sequence from K289_3 as presently determined is reported in SEQ ID NO:10. What applicants believe is the proper reading frame and the predicted amino acid sequence encoded by such internal sequence is reported in SEQ ID NO:11. Amino acids 1 to 20 of SEQ ID NO:11 are a predicted leader/signal sequence, with the predicted mature amino acid sequence beginning at amino acid 21. Additional nucleotide sequence from the 3' portion of K289_3, including the polyA tail, is reported in SEQ ID NO:12.

The nucleotide sequence disclosed herein for K289_3 was searched against the GenBank database using BLASTA/BLASTX and FASTA search protocols. K289_3 demonstrated at least some identity with ESTs identified as "me82d12.r1 Soares mouse embryo NbME13.5 14.5 Mus musculus" (W77682, BlastN/Fasta) "MDB0966 Mus musculus cDNA 3' end" (R75054, BlastN). Based upon identity, K289_3 proteins and each identical protein or peptide may share at least some activity.

Clone "K322_2"

A polynucleotide of the present invention has been identified as clone "K322_2". K322_2 was isolated from a murine bone marrow (stromal cell line FCM-4) cDNA library using methods which are selective for cDNAs encoding secreted proteins. K322_2 is a full-length clone, including the entire coding sequence of a secreted protein (also referred to herein as "K322_2 protein").

The nucleotide sequence of the 5' portion of K322_2 as presently determined is reported in SEQ ID NO:13. An additional internal nucleotide sequence from K322_2 as presently determined is reported in SEQ ID NO:14. What applicants believe is the proper reading frame and the predicted amino acid sequence encoded by such internal sequence is reported in SEQ ID NO:15. Amino acids 1 to 27 of SEQ ID NO:15 are a predicted leader/signal sequence, with the predicted mature amino acid sequence beginning at amino acid 28. Additional nucleotide sequence from the 3' portion of K322_2, including the polyA tail, is reported in SEQ ID NO:16.

The nucleotide sequence disclosed herein for K322_2 was searched against the GenBank database using BLASTA/BLASTX and FASTA search protocols. K322_2 demonstrated at least some identity with "mb55a11.r1 Soares mouse p3NMF19.5 Mus musculus cDNA" (W15869, BlastN). Based upon identity, K322_2 proteins and each identical protein or peptide may share at least some activity.

Deposit of Clones

Clones BG511_30, BL15_1, K289_3 and K322_2 were deposited on Aug. 1, 1996 with the American Type Culture Collection under accession number ATCC 98117, from which each clone comprising a particular polynucleotide is obtainable. Each clone has been transfected into separate bacterial cells (*E. coli*) in this composite deposit. Each clone can be removed from the vector in which it was deposited by performing an EcoRI/NotI digestion (5' cite, EcoRI; 3' cite, NotI) to produce the appropriately sized fragment for such clone (approximate clone size fragment are identified below). Bacterial cells containing a particular clone can be obtained from the composite deposit as follows:

An oligonucleotide probe or probes should be designed to the sequence that is known for that particular clone. This sequence can be derived from the sequences provided herein, or from a combination of those sequences. The sequence of the oligonucleotide probe that was used to isolate each full-length clone is identified below, and should be most reliable in isolating the clone of interest.

| Clone | Probe Sequence |
|---|---|
| BG511_30 | SEQ ID NO:17 |
| BL15_1 | SEQ ID NO:18 |
| K289_3 | SEQ ID NO:19 |
| K322_2 | SEQ ID NO:20 |

In the sequences listed above which include an N at position 2, that position is occupied in preferred probes/primers by a biotinylated phosphoaramidite residue rather than a nucleotide (such as, for example, that produced by use of biotin phosphoramidite (1 -dimethoxytrityloxy-2-(N-biotinyl-4-aminobutyl)-propyl-3 -O-(2-cyanoethyl)-(N,N-diisopropyl) -phosphoramadite) (Glen Research, cat. no. 10-1953)).

The design of the oligonucleotide probe should preferably follow these parameters:

(a) It should be designed to an area of the sequence which has the fewest ambiguous bases ("N's"), if any;

(b) It should be designed to have a $T_m$ of approx. 80° C. (assuming 2° for each A or T and 4 degrees for each G or C).

The oligonucleotide should preferably be labeled with g-$^{32}$P ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4e+6 dpm/pmole.

The bacterial culture containing the pool of full-length clones should preferably be thawed and 100 μl of the stock used to inoculate a sterile culture flask containing 25 ml of sterile L-broth containing ampicillin at 100 μg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 μg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65° C. for 1 hour with gentle agitation in 6X SSC (20X stock is 175.3 g NaCl/liter, 88.2 g Na citrate/liter, adjusted to pH 7.0 with NaOH) containing 0.5% SDS, 100 μg/ml of yeast RNA, and 10 mM EDTA (approximately 10 mL per 150 mm filter). Preferably, the probe is then added to the hybridization mix at a concentration greater than or equal to 1e+6 dpm/mL. The filter is then preferably incubated at 65° C. with gentle agitation overnight. The filter is then preferably washed in 500 mL of 2X SSC/0.5% SDS at room temperature without agitation, preferably followed by 500 mL of 2X SSC/0.1% SDS at room temperature with gentle shaking for 15 minutes. A third wash with 0.1X SSC/0.5% SDS at 65° C. for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides both full-length and mature forms of the disclosed proteins. The full-length form of the such proteins is identified in the sequence listing by translation of the nucleotide sequence of each disclosed clone. The mature form of such protein may be obtained by expression of the disclosed full-length polynucleotide (preferably those deposited with ATCC) in a suitable mammalian cell or other host cell. The sequence of the mature form of the protein may also be determinable from the amino acid sequence of the full-length form.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

Where the protein of the present invention is membrane-bound (e.g., is a receptor), the present invention also provides for soluble forms of such protein. In such forms part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information.

Species homologs of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence. A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae*, *Schizosaccharomyces pombe*, Kluyveromyces strains, Candida, or any yeast strain capable of expressing heterologous proteins. Potentially suitable bacterial strains include *Escherichia coli*, *Bacillus subtilis*, *Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No. 1555* (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

USES AND BIOLOGICAL ACTIVITY

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152: 1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In *Current Protocols in Immunology*. J.E.e.a. Coligan eds. Vol 1 pp. 3.12.1–3.12.14, John Wiley and Sons, Toronto. 1994; and Measurement of mouse and human Interferon γ, Schreiber, R. D. In *Current Protocols in Immunology*. J.E.e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology*. J.E.e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In *Current Protocols in Immunology*. J.E.e.a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11—Bennett, F., Giannotti, J., Clark, S. C. and Turner, K. J. In *Current Protocols in Immunology*. J.E.e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In *Current Protocols in Immunology*. J.E.e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitis, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I α chain protein and $β_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028:3033, 1990; and Assays for B cell function: In vitro antibody production, Mond, J. J. and Brunswick, M. In *Current Protocols in Immunology*. J.E.e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney. M. G. In *Culture of Hematopoietic Cells*. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In *Culture of Hematopoietic Cells*. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In *Culture of Hematopoietic Cells*. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In *Culture of Hematopoietic Cells*. R. I. Freshney, et al. eds. Vol pp. 163–179, Wiley-Liss, Inc., New York, N.Y. 1994; Long term culture initiating cell assay, Sutherland, H. J. In *Culture of Hematopoietic Cells*. R. I. Freshney, et al. eds. Vol pp. 139–162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *Epidermal Wound Healing*, pps. 71–112 (Maibach, H. I. and Rovee, D. T., eds.), Year Book Medical Publishers, Inc., Chicago, as modified by Eaglstein and Mertz, J. Invest. Dermatol 71:382–84 (1978).

Activin/Inhibin Activity

A protein of the present invention may also exhibit activin- or inhibin-related activities. Inhibins are characterized by their ability to inhibit the release of follicle stimulating hormone (FSH), while activins are and are characterized by their ability to stimulate the release of follicle stimulating hormone (FSH). Thus, a protein of the present invention, alone or in heterodimers with a member of the inhibin α family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25: 1744–1748; Gruber et al. J. of Immunol. 152:5860–5867, 1994; Johnston et al. J. of Immunol. 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Liner et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

ADMINISTRATION AND DOSING

A protein of the present invention (from whatever source derived, including without limitation from recombinant and non-recombinant sources) may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunolgobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 µg to about 100 mg (preferably about 0.1 µg to about 10 mg, more preferably about 0.1 µg to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells.

In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of vital vectors or naked DNA).

Cells may also be cultured ex vivo in the presence of proteins of the present invention in order to proliferate or to produce a desired effect on or activity in such cells. Treated cells can then be introduced in vivo for therapeutic purposes.

Patent and literature references cited herein are incorporated by reference as if fully set forth.

---

What is claimed is:

1. An isolated polynucleotide selected from the group consisting of:
   (a) a polynucleotide comprising the nucleotide sequence of SEQ ID NO:2;
   (b) a polynucleotide comprising the nucleotide sequence of SEQ ID NO:2 from nucleotide 272 to nucleotide 424;
   (c) a polynucleotide comprising the nucleotide sequence of SEQ ID NO:2 from nucleotide 395 to nucleotide 424;
   (d) a polynucleotide comprising the nucleotide sequence of the full length protein coding sequence of clone BG511_30 deposited under accession number ATCC 98117;
   (e) a polynucleotide encoding the full length protein encoded by the cDNA insert of clone BG511_30 deposited under accession number ATCC 98117;
   (f) a polynucleotide comprising the nucleotide sequence of the mature protein coding sequence of clone BG511_30 deposited under accession number ATCC 98117;
   (g) a polynucleotide encoding the mature protein encoded by the cDNA insert of clone BG511_30 deposited under accession number ATCC 98117;
   (h) a polynucleotide encoding a protein comprising the amino acid sequence of SEQ ID NO:3;
   (i) a polynucleotide encoding a protein comprising the amino acid sequence of SEQ ID NO:3 from amino acid 42 to amino acid 51; and
   (j) a polynucleotide which is an allelic variant of a polynucleotide of (a)–(g) above.

2. An isolated polynucleotide of claim 1 wherein said polynucleotide is operably linked to an expression control sequence.

3. A host cell transformed with a polynucleotide of claim 2.

4. The host cell of claim 3, wherein said cell is a mammalian cell.

5. A process for producing a protein encoded by a polynucleotide of claim 2, which process comprises:
   (a) growing a culture of the host cell of claim 3 in a suitable culture medium; and
   (b) purifying said protein from the culture.

6. A protein produced according to the process of claim 5.

7. The protein of claim 6 comprising a mature protein.

8. An isolated protein, wherein said protein comprises an amino acid sequence selected from the group consisting of:
   (a) the amino acid sequence of SEQ ID NO:3;
   (b) the amino acid sequence of SEQ ID NO:3 from amino acid 42 to amino acid 51; and
   (c) the amino acid sequence encoded by the cDNA insert of clone BG511_30 deposited under accession number ATCC 98117;

the protein being substantially free from other mammalian proteins.

9. The protein of claim 8, wherein said protein comprises the amino acid sequence of SEQ ID NO:3.

10. A composition comprising the protein of claim 8, and a pharmaceutically acceptable carrier.

11. An isolated gene corresponding to the cDNA sequence of SEQ ID NO:2, SEQ ID NO:1 and SEQ ID NO:4.

12. The protein of claim 8, wherein said protein comprises the amino acid sequence of SEQ ID NO:3 from amino acid 42 to amino acid 51.

13. The polynucleotide of claim 1, wherein said polynucleotide comprises the nucleotide sequence of SEQ ID NO:2.

14. The polynucleotide of claim 1, wherein said polynucleotide comprises the nucleotide sequence of SEQ ID NO:2 from nucleotide 272 to nucleotide 424.

15. The polynucleotide of claim 1, wherein said polynucleotide comprises the nucleotide sequence of SEQ ID NO:2 from nucleotide 395 to nucleotide 424.

16. The polynucleotide of claim 1, wherein said polynucleotide comprises the nucleotide sequence of the full length protein coding sequence of clone BG511_30 deposited under accession number ATCC 98117.

17. The polynucleotide of claim 1, wherein said polynucleotide comprises a polynucleotide encoding the full length protein encoded by the cDNA insert of clone BG511_30 deposited under accession number ATCC 98117.

18. The polynucleotide of claim 1, wherein said polynucleotide comprises the nucleotide sequence of the mature protein coding sequence of clone BG511_30 deposited under accession number ATCC 98117.

19. The polynucleotide of claim 1, wherein said polynucleotide comprises a polynucleotide encoding the mature protein encoded by the cDNA insert of clone BG511_30 deposited under accession number ATCC 98117.

20. The polynucleotide of claim 1, wherein said polynucleotide comprises a polynucleotide encoding a protein comprising the amino acid sequence of SEQ ID NO:3.

21. The polynucleotide of claim 1, wherein said polynucleotide comprises a polynucleotide encoding a protein comprising the amino acid sequence of SEQ ID NO:3 from amino acid 42 to amino acid 51.

* * * * *